(12) United States Patent
Gunderson

(10) Patent No.: US 9,533,165 B1
(45) Date of Patent: Jan. 3, 2017

(54) DETECTION OF MEDICAL ELECTRICAL LEAD ISSUES AND THERAPY CONTROL

(71) Applicant: Medtronic, Inc., Minneapolis, MN (US)

(72) Inventor: Bruce D. Gunderson, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/829,697

(22) Filed: Aug. 19, 2015

(51) Int. Cl.
*A61N 1/39* (2006.01)

(52) U.S. Cl.
CPC ........... *A61N 1/3931* (2013.01); *A61N 1/3956* (2013.01); *A61N 1/3987* (2013.01)

(58) Field of Classification Search
None
See application file for complete search history.

(56) References Cited

U.S. PATENT DOCUMENTS

| | | | |
|---|---|---|---|
| 5,354,316 A | 10/1994 | Keimel | |
| 5,507,782 A | 4/1996 | Kieval et al. | |
| 5,545,186 A | 8/1996 | Olson et al. | |
| 6,393,316 B1 | 5/2002 | Gillberg et al. | |
| 6,892,092 B2 | 5/2005 | Palreddy et al. | |
| 7,031,771 B2 | 4/2006 | Brown et al. | |
| 7,289,851 B2 | 10/2007 | Gunderson et al. | |
| 7,467,009 B2 | 12/2008 | Palreddy et al. | |
| 7,783,354 B2 | 8/2010 | Gunderson | |
| 7,974,690 B2 | 7/2011 | Kracker | |
| 8,078,277 B2 | 12/2011 | Gunderson et al. | |
| 8,160,684 B2 | 4/2012 | Ghanem et al. | |
| 8,437,842 B2 | 5/2013 | Zhang et al. | |
| 8,521,276 B2 | 8/2013 | Sweeney et al. | |
| 8,712,523 B2 | 4/2014 | Sanghera et al. | |
| 8,744,556 B2 | 6/2014 | Majajan et al. | |
| 8,781,585 B2 | 7/2014 | Gunderson et al. | |
| 8,792,971 B2 | 7/2014 | Gunderson et al. | |
| 8,849,385 B2 | 9/2014 | Kracker | |
| 8,942,795 B2 | 1/2015 | Gunderson et al. | |
| 2008/0161870 A1 | 7/2008 | Gunderson | |
| 2008/0161872 A1 | 7/2008 | Gunderson | |
| 2008/0172098 A1 | 7/2008 | Gunderson | |
| 2010/0023084 A1* | 1/2010 | Gunderson | A61N 1/3706 607/28 |
| 2011/0196247 A1 | 8/2011 | Cao et al. | |

* cited by examiner

*Primary Examiner* — Brian T Gedeon

(57) ABSTRACT

An implantable medical device is configured to detect saturation events from a cardiac electrical signal, detect a tachyarrhythmia based at least in part on the cardiac electrical signal, responsive to detecting the tachyarrhythmia, and compare the detected saturation events to lead issue criteria. If the detected saturation events satisfy lead issue criteria, a therapy for treating the tachyarrhythmia is withheld by the implantable medical device.

23 Claims, 8 Drawing Sheets

DETECTION OF MEDICAL ELECTRICAL LEAD ISSUES AND THERAPY CONTROL

TECHNICAL FIELD

The disclosure relates to implantable medical devices and associated methods for detecting medical electrical lead issues and controlling delivery of an electrical stimulation therapy in response to detecting a lead issue.

BACKGROUND

A variety of implantable medical devices (IMDs) for delivering a therapy, monitoring a physiological condition of a patient or a combination thereof have been clinically implanted or proposed for clinical implantation in patients. Some IMDs may employ one or more elongated electrical leads carrying stimulation electrodes, sense electrodes, and/or other sensors.

IMDs may deliver therapy to and/or monitor conditions of a variety of organs, nerves, muscle or tissue, such as the heart, brain, stomach, spinal cord, pelvic floor, or the like. Some IMDs, such as cardiac pacemakers or implantable cardioverter defibrillators (ICDs) monitor a patient's heart activity by sensing cardiac electrical signals to detect an abnormal rhythm. Pacemakers and ICDs may provide therapeutic electrical stimulation to the heart of the patient via electrodes carried by a medical electrical lead coupled to the pacemaker or ICD. The electrical stimulation may include pacing pulses to address abnormal cardiac rhythms such as bradycardia and ventricular tachycardia or cardioversion/defibrillation shocks for treating malignant forms of ventricular tachycardia and ventricular fibrillation. The reliability of an IMD in delivering electrical stimulation pulses to treat abnormal rhythms and sensing electrical physiological signals for monitoring a patient depends at least in part on the integrity of the insulation and the electrical conductors of the medical electrical lead that carries electrodes used for delivering the therapeutic stimulation pulses and for sensing physiological signals.

SUMMARY

In general, the disclosure is directed to techniques for detecting medical electrical lead issues and withholding therapy delivered by an IMD if a lead issue is detected. An IMD capable of sensing cardiac electrical signals from and delivering electrical stimulation pulses to a patient's heart as disclosed herein detects a medical electrical lead issue by analyzing the cardiac electrical signal for saturation events. The IMD withholds delivery of an electrical stimulation pulse when saturation events satisfy lead issue detection criteria.

In one example, the disclosure provides an implantable medical device including sensing circuitry to receive a cardiac electrical signal via electrodes carried by a medical electrical lead when the medical electrical lead is coupled to the implantable medical device, therapy delivery circuitry to deliver a tachyarrhythmia therapy to a patient's heart; and a control module coupled to the sensing module and the therapy delivery module. The control module is configured to detect saturation events from the cardiac electrical signal, detect a tachyarrhythmia based at least in part on the cardiac electrical signal, responsive to detecting the tachyarrhythmia, compare the detected saturation events to lead issue criteria, and withhold the tachyarrhythmia therapy when the lead issue criteria are satisfied.

In another example, the disclosure provides a method including receiving a cardiac electrical signal by sensing circuitry of an implantable medical device via electrodes carried by a medical electrical lead when the medical electrical lead is coupled to the implantable medical device, detecting saturation events from the cardiac electrical signal by a control module of the implantable medical device, detecting a tachyarrhythmia by the control module based at least in part on the cardiac electrical signal, responsive to detecting the tachyarrhythmia, comparing the detected saturation events to lead issue criteria; and withholding a tachyarrhythmia therapy when the lead issue criteria are satisfied.

In another example, the disclosure provides a non-transitory computer readable storage medium comprising instructions which when executed by a processor of an implantable medical device cause the implantable medical device to detect saturation events from a cardiac electrical signal received by the implantable medical device via electrodes carried by a medical electrical lead when the medical electrical lead is coupled to the implantable medical device, detect a tachyarrhythmia based at least in part on the cardiac electrical signal, responsive to detecting the tachyarrhythmia, compare the detected saturation events to lead issue criteria; and withhold a tachyarrhythmia therapy when the lead issue criteria are satisfied.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

In general, an implantable medical device (IMD) is disclosed that is configured to sense cardiac electrical signals and deliver cardiac electrical stimulation therapies using electrodes coupled to the IMD via a medical electrical lead. The IMD is configured to detect lead issues, e.g., due to an insulation breach, electrical conductor fracture, or poor connection between a lead connector and IMD connector assembly, by analyzing the sensed cardiac electrical signal for saturation events.

Figure 1:
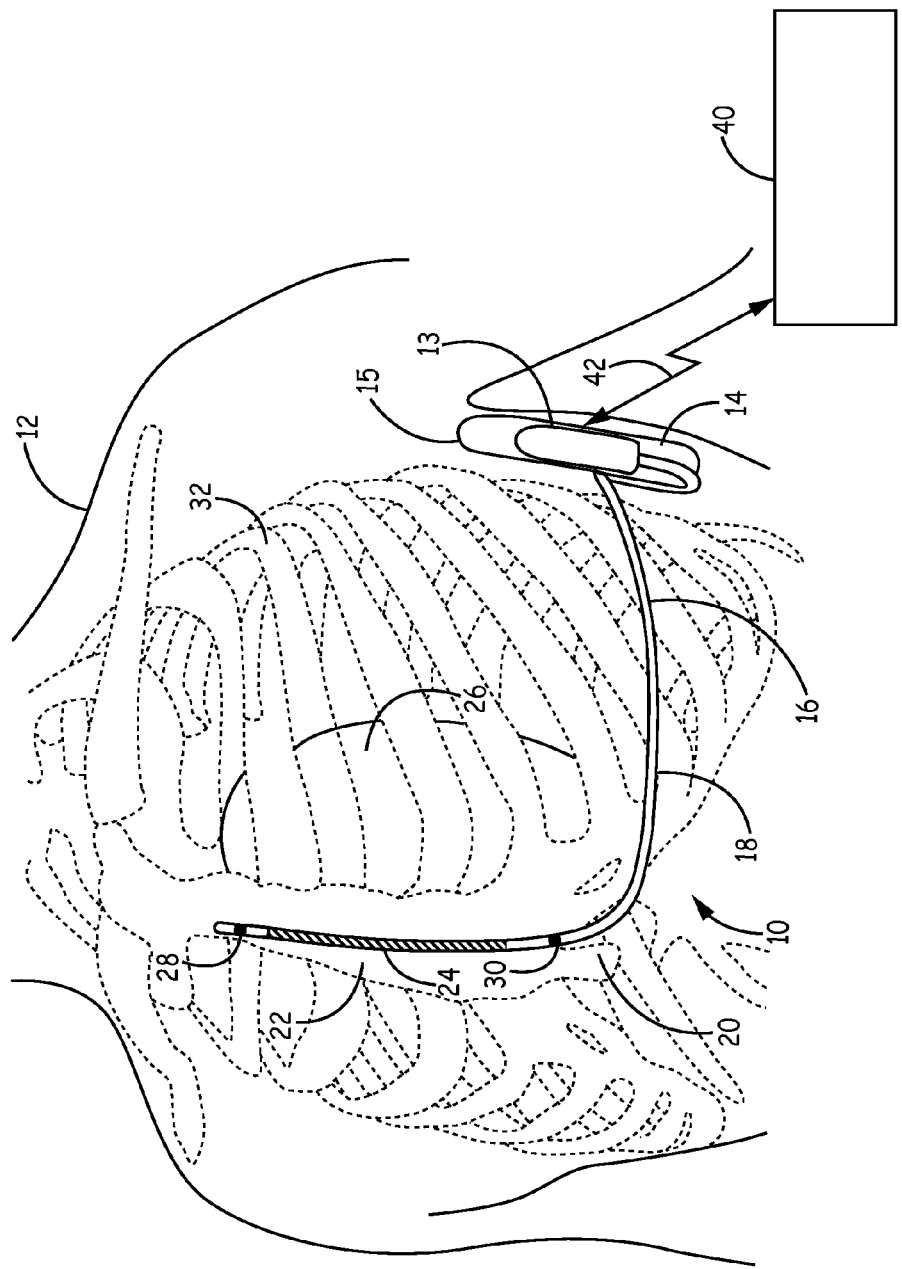
FIG. 1 is a conceptual diagram illustrating an IMD system used to sense cardiac electrical signals and provide therapy to a patient's heart.

FIG. 1 is a conceptual diagram illustrating an IMD system 10 used to sense cardiac electrical signals in patient 12 and provide therapy to heart 26. IMD system 10 includes an ICD 14 coupled to an extravascular defibrillation lead 16. ICD 14 is implanted subcutaneously on the left side of patient 12. Defibrillation lead 16, which is connected to ICD 14, extends medially from ICD 14 toward sternum 22 and xiphoid process 20 of patient 12. At a location near xiphoid process 20 defibrillation lead 16 bends or turns and extends subcutaneously superior, substantially parallel to sternum 22. Defibrillation lead 16 may be implanted such that lead 16 is offset laterally to the left side of the body of sternum 22 (e.g., towards the left side of patient 12), offset to the right of sternum 22 or over sternum 22.

Defibrillation lead 16 includes a defibrillation electrode 24, which may be an elongated coil electrode, and a pair of sensing electrodes 28 and 30. Defibrillation lead 16 is placed along sternum 22 such that a therapy vector between defibrillation electrode 24 and the housing 15 of ICD 14 is substantially across one or both ventricles of heart 26. In other examples, another electrode along lead 16 or along a second lead coupled to ICD 14 may be used in combination with defibrillation electrode 24 for delivering a shock therapy.

In the example illustrated in FIG. 1, lead 16 is implanted subcutaneously, e.g., between the skin and the ribs or sternum. Lead 16 is advanced suprasternally remaining external to the thoracic cavity. In other embodiments, lead 16 may be advanced substernally or within ribcage 32, e.g., intra-thoracically. For example, lead 16 may be implanted at least partially in a substernal location. In such a configuration, a portion of lead 16 may extend subcutaneously from ICD 14 toward sternum 22 and at least a portion of lead 16 (e.g., the portion containing electrodes 24, 28, and 30) is advanced under or below the sternum in the mediastinum and, more particularly, in the anterior mediastinum. Lead 16 may be at least partially implanted in other intrathoracic locations, e.g., locations in and around heart 26, with or without making direct contact with the outer surface of heart 26, e.g., in epicardial or pericardial locations. In still other examples, lead 16 may be embodied as a transvenous, intracardiac lead that is advanced transvenously to position one or more electrodes within a patient's heart or its vasculature. An example of an ICD coupled to transvenous medical electrical leads is described below in conjunction with FIG. 3.

Although ICD 14 is illustrated in FIG. 1 as being implanted near a midaxillary line of patient 12, ICD 14 may also be implanted at other subcutaneous locations of patient 12, such as further posterior on the torso toward the posterior axillary line, further anterior on the torso toward the anterior axillary line, in a pectoral region, or at other locations of patient 12. In instances in which ICD 14 is implanted pectorally, lead 16 may follow a different path, e.g., across the upper chest area and inferior along sternum 22. When the ICD 14 is implanted in the pectoral region, lead 16 or a second lead including a defibrillation electrode may extend along the left side of the patient such that a defibrillation electrode is located along the left side of the patient to function as an anode or cathode of a therapy vector for defibrillating heart 26.

The techniques disclosed herein are not limited to a particular implant location of ICD 14 or medical electrical lead 16 coupled to ICD 14. Rather, the disclosed techniques for detecting a lead issue may be implemented in any IMD that is coupled to a medical electrical lead, configured to sense electrical signals, and is implanted at any desired anatomical location appropriate for a given medical application.

ICD 14 includes a housing 15 that forms a hermetic seal that protects electronic circuitry and other components within ICD 14. The housing 15 of ICD 14 may be formed of a conductive material, such as titanium or other biocompatible conductive material or a combination of conductive and non-conductive materials. In some instances, the housing 15 functions as an electrode (sometimes referred to as a housing electrode or "can" electrode) that is used in combination with one of electrodes 24, 28 and 30 to deliver a therapy to heart 26 or to sense electrical activity of heart 26.

ICD 14 includes a connector assembly 13 (sometimes referred to as a connector block or header) for receiving a proximal connector (not illustrated) of lead 16. Connector assembly 13 includes electrical feedthroughs through which electrical connections are made between electrical conductors within defibrillation lead 16 and electronic components included within the housing.

Defibrillation lead 16 includes an elongated lead body 18 having a proximal end that includes a connector configured to mate with connector assembly 13 of ICD 14 and a distal portion that includes electrodes 24, 28 and 30. The lead body 18 of defibrillation lead 16 may be formed from a non-conductive, e.g., electrically insulating material, including silicone, polyurethane, fluoropolymers, mixtures thereof, or other appropriate materials, and is shaped to form one or more lumens within which the one or more electrical conductors (not illustrated) each extend to respective ones of electrodes 24, 28 and 30.

When the connector at the proximal end of defibrillation lead 16 is connected to connector assembly 13, the respective electrical conductors electrically couple to circuitry of ICD 14, such as a therapy delivery circuitry and a sensing circuitry via connections in connector assembly 13, including associated feedthroughs. The electrical conductors transmit electrical stimulation pulses from a therapy delivery circuitry within ICD 14 to one or more of electrodes 24, 28 and 30 and transmit sensed electrical signals from one or more of electrodes 24, 28 and 30 to the sensing circuitry within ICD 14. Although defibrillation lead 16 is illustrated as including three electrodes 24, 28 and 30, defibrillation lead 16 may include more or fewer electrodes. For example, two or more sensing electrodes may be included for sensing a cardiac electrical signal, e.g., a subcutaneous electrocardiogram (ECG) signal.

ICD 14 may sense electrical activity of heart 26 from an ECG signal acquired via one or more sensing vectors that include combinations of electrodes 28 and 30 and housing 15. For example, ICD 14 may obtain ECG signals using a sensing vector between electrodes 28 and 30, between electrode 28 and housing 15, between electrode 30 and housing 15, or any combination thereof. In some instances, ICD 14 may even sense cardiac electrical signals using a sensing vector that includes defibrillation electrode 24, such as a sensing vector between defibrillation electrode 24 and one of electrodes 28 and 30, or a sensing vector between defibrillation electrode 24 and the housing 15.

A lead performance issue may arise if the electrical insulation of a conductor extending to one of electrodes 24, 28 or 30 is breached, if one of the conductors extending through lead body 18 is fractured, or if the electrical connection between the lead connector and ICD connector assembly 13 is compromised. An ECG received by ICD 14 may include saturation events due to a lead issue. ICD 14 is configured to detect ECG signal saturation events, track saturation events using a time stamp and/or counter, and detect a lead issue when occurrences of saturation events satisfy lead issue detection criteria.

ICD 14 analyzes acquired ECG signals to detect ventricular tachyarrhythmias (VT), which may include both ventricular tachycardia and ventricular fibrillation, and in response to detecting VT may generate and deliver an electrical therapy to heart 26. For example, ICD 14 may deliver one or more defibrillation shocks via a therapy vector that includes defibrillation electrode 24 and the housing 15. In some instances, ICD 14 may be configured to deliver one or more pacing therapies, such as anti-tachycardia pacing (ATP) post shock pacing. Oversensing of electrical noise due to a lead issue could lead to a false detection of VT and/or impact therapy delivery. Accordingly, ICD 14 is configured to detect a lead issue based on occurrences of ECG signal saturation events and withhold a scheduled cardioversion/defibrillation (CV/DF) shock therapy in response to detecting the lead issue. ICD 14 may be capable of generating an alert that may be transmitted as a wireless telemetry communication signal to external device 40 to alert patient 12 or a clinician of the detected lead issue. In other examples, the alert may be an audible sound or mild electrical stimulation generated by ICD 14 and perceived by the patient.

ICD 14 is capable of bidirectional wireless communication with an external device 40. External device 40 is often referred to as a "programmer" because it is typically used by a physician, technician, nurse, clinician or other qualified user for programming operating parameters in ICD 14. Operating parameters, such as sensing and therapy delivery control parameters, may be programmed into ICD 14 using external device 40. External device 40 may be located in a clinic, hospital or other medical facility. External device 40 may alternatively be embodied as a home monitor or a handheld device that may be used in a medical facility, in the patient's home, or another location. Aspects of external device 40 may generally correspond to the external programming/monitoring unit disclosed in U.S. Pat. No. 5,507,782 (Kieval, et al.), hereby incorporated herein by reference in its entirety.

External device 40 may be used to program operating parameters, such as sensing control parameters, tachyarrhythmia detection control parameters, and therapy delivery control parameters used by ICD 14. External device 40 may display programming data and information relating to ICD 14 functions to a user for reviewing ICD operation and programmed parameters as well as ECG signals or other physiological data that are retrieved from ICD 14 during an interrogation session.

External device 40 establishes a wireless radio frequency (RF) communication link 42 with an implantable telemetry circuitry included in ICD 14 for sending and receiving data via communication link 42. Communication link 42 may be established between ICD 14 and external device 40 via a radio frequency (RF) link in the Medical Implant Communication Service (MICS) band, Medical Data Service (MEDS) band, BLUETOOTH® wireless communication standard, Wi-Fi or other RF bandwidth.

External device 40 may be capable of bi-directional communication with ICD 14 over a wide range of distances, e.g., up to approximately 10 meters. In other examples, telemetry communication with ICD 14 may require the use of a programming head placed in proximity of ICD 14 to facilitate data transfer. It is contemplated that external device 40 may be in wired or wireless connection to a communications network for transferring data to a remote database or computer to allow remote management of ICD 14.

Figure 2:
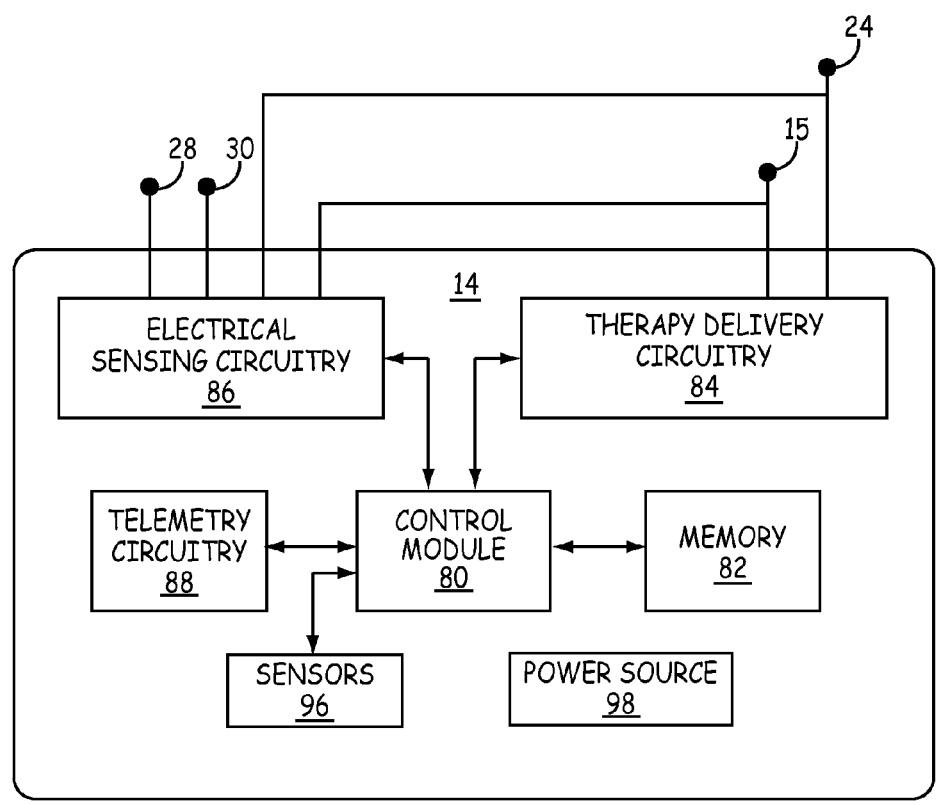
FIG. 2 is a schematic diagram of an ICD according to one example.

FIG. 2 is a schematic diagram of ICD 14 according to one example. The electronic circuitry enclosed within housing 15 includes software, firmware and hardware that cooperatively monitor one or more ECG signals, determine when a CV/DF shock is necessary, and deliver prescribed CV/DF therapies. ICD 14 is coupled to a lead, such as lead 16 shown in FIG. 1, carrying electrodes, such as electrodes 24, 28 and 30, positioned in operative relation to the patient's heart for sensing cardiac electrical signals and delivering therapeutic electrical stimulation, e.g., CV/DF shocks and post-shock pacing during recovery.

ICD 14 includes control module 80, memory 82, therapy delivery circuitry 84, electrical sensing circuitry 86, and telemetry circuitry 88. A power source 98 provides power to the circuitry of ICD 14, including each of the modules 80, 82, 84, 86, 88, and 90 as needed. Power source 98 may include one or more energy storage devices, such as one or more rechargeable or non-rechargeable batteries.

The functional blocks shown in FIG. 2 represent functionality that may be included in ICD 14 and may include any discrete and/or integrated electronic circuit components that implement analog and/or digital circuits capable of producing the functions attributed to ICD 14 herein. For example, the modules and/or circuitry may include analog circuits, e.g., amplification circuits, filtering circuits, and/or other signal conditioning circuits. The modules and/or circuitry may also include one or more digital circuits, e.g., analog-to-digital converters, combinational or sequential logic circuits, integrated circuits, processors, application specific integrated circuits (ASICs), digital signal processors (DSP), field programmable gate arrays (FPGA), programmable logic controller (PLC), complex programmable logic device (CPLD), memory devices, etc.

Memory 82 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control module 80 or other ICD modules to perform various functions attributed to ICD 14. The non-transitory computer readable media storing the instructions may include any of the media listed above, with the sole exception being a transitory propagating signal.

The functional operation of ICD 14 as disclosed herein should not be construed as reflective of a specific form of software or hardware necessary to practice the methods described. It is believed that the particular form of software, hardware and/or firmware will be determined primarily by the particular system architecture employed in ICD 14. Providing software, hardware, and/or firmware to accomplish the described functionality in the context of any modern IMD, given the disclosure herein, is within the abilities of one of skill in the art.

Control module 80 communicates with therapy delivery circuitry 84 and electrical sensing circuitry 86 for sensing cardiac electrical activity, detecting cardiac rhythms, and generating electrical stimulation therapies in response to sensed signals. Therapy delivery circuitry 84 is electrically coupled to defibrillation electrode 24 and housing 15 for delivering electrical stimulation therapies such as CV/DF shocks. In some examples, depending on the intended implant location of electrodes 28 and 30, therapy delivery circuitry 84 may additionally be coupled to electrodes 28 and 30 for use in delivering therapy and/or delivering mild electrical stimulation for generating a patient alert.

Electrical sensing circuitry 86 is electrically coupled to electrodes 24, 28, and 30 carried by lead 16 (shown in FIG. 1) and housing 15, which may serve as a common or ground electrode. Electrical sensing circuitry 86 is selectively coupled to sensing electrodes 28, 30 and housing 15 in order to monitor electrical activity of the patient's heart. Electrical sensing circuitry 86 may additionally be selectively coupled to defibrillation electrode 24. Sensing circuitry 86 may be enabled to monitor one or more sensing vectors selected from the available electrodes 24, 28, 30 and 15. For example, sensing circuitry 86 may include switching circuitry for selecting which of electrodes 24, 28, 30 and housing 15 are coupled to sense amplifiers or other cardiac event detectors included in sensing circuitry 86. Switching circuitry may include a switch array, switch matrix, multiplexer, or any other type of switching device suitable to selectively couple sense amplifiers to selected electrodes.

In some examples, electrical sensing circuitry 86 includes multiple sensing channels for sensing multiple ECG sensing vectors selected from electrodes 24, 28, 30 and housing 15. For example, sensing circuitry 86 may include two sensing channels. Each sensing channel may include a sense amplifier or other cardiac event detection circuitry for sensing cardiac events, e.g., R-waves, from the received ECG signal developed across the selected electrodes 24, 28, 30 or 15. The cardiac event detector may operate using an auto-adjusting sensing threshold set based on a peak amplitude of a currently sensed event that may decay over time. Each time the received ECG signal crosses the auto-adjusting sensing threshold outside an absolute blanking period, a cardiac sensed event signal, such as an R-wave sensed event signal, is produced and passed to control module 80 for use in detecting VT.

Control module 80 is configured to detect VT episodes that may be life-threatening if left untreated, generally referred to herein as a "shockable rhythm," such as non-sinus, fast ventricular tachycardia or ventricular fibrillation. The timing of R-wave sensed event signals received from sensing circuitry 86 may be used by control module 80 to determine RR intervals between cardiac sensed event signals. Control module 80 may count RR intervals that fall into different rate detection zones for determining a ventricular rate or performing other rate- or interval-based assessments for detecting VT and discriminating VT from rhythms that do not require a CV/DF shock.

Sensing circuitry 86 may include an analog-to-digital converter for providing a digital ECG signal from one or all available sensing channels to control module 80 for further signal analysis for use in VT detection. A sensed ECG signal may be converted to a multi-bit digital signal by sensing circuitry 86 and provided to control module 80 for performing ECG morphology analysis. Analysis of the ECG signal morphology may be performed for detecting, confirming or discriminating VT.

Examples of algorithms that may be performed by ICD 14 for detecting, discriminating and treating shockable rhythms are generally disclosed in U.S. Pat. No. 5,354,316 (Keimel); U.S. Pat. No. 5,545,186 (Olson, et al.); U.S. Pat. No. 6,393,316 (Gillberg et al.); U.S. Pat. No. 7,031,771 (Brown, et al.); U.S. Pat. No. 8,160,684 (Ghanem, et al.), and U.S. Pat. No. 8,437,842 (Zhang, et al.), all of which patents are incorporated herein by reference in their entirety. The detection algorithms are highly sensitive and specific for the presence or absence of life threatening, shockable VT. Methods disclosed herein for detecting a lead issue may be implemented in any of the IMDs described as being coupled to a medical electrical lead in the incorporated references.

It should be noted that implemented arrhythmia detection algorithms may utilize not only ECG signal analysis methods but may also utilize supplemental sensors 96, such as blood pressure, tissue oxygenation, respiration, patient activity, heart sounds, and the like, for contributing to a decision by control module 80 to apply or withhold a therapy.

In some examples, analysis of the ECG signal by control module 80 is performed to detect saturation events of the ECG signal and determine if occurrences of saturation events satisfy lead issue detection criteria. In other examples, electrical sensing circuitry 86 may be configured to pass a saturation event signal to control module 80 when the input to an amplifier or AD converter of sensing circuitry 86 is over range in either a positive or negative direction. Control module 80 may store a time and date stamp for each saturation event signal in memory 82 and/or track saturation events using counters and evaluate the occurrences of the saturation events for detecting a lead issue as described below.

Therapy delivery circuitry 84 includes a high voltage (HV) therapy delivery circuitry including one or more HV output capacitors and, in some instances, a low voltage therapy delivery circuitry. When a shockable VT rhythm is detected, control module 80 may evaluate detected saturation events to determine whether a lead issue is detected, which may have led to the VT detection due to oversensing of electrical noise. If a lead issue is detected, charging of the HV output capacitors and shock delivery is withheld. If saturation events do not meet lead issue detection criteria, control module 80 controls therapy delivery circuitry 84 to proceed with shock delivery. The HV capacitors are charged to a pre-programmed voltage level by a HV charging circuit. Control module 80 applies a signal to trigger discharge of the HV capacitors upon detecting a feedback signal from therapy delivery circuitry 84 that the HV capacitors have reached the voltage required to deliver a programmed shock energy. In this way, control module 80 controls operation of the high voltage output circuit of therapy delivery circuitry 84 to deliver high energy cardioversion/defibrillation shocks using defibrillation electrode 24 and housing 15.

Control module 80 may be configured to generate a patient or physician alert in response to lead issue detection criteria being met or other lead integrity conditions being detected. The alert may be a communication signal transmitted by telemetry circuitry 88, mild electrical stimulation delivered by therapy delivery circuitry 84 via any of electrodes 24, 28, 30 or 15, an audible alert generated by an acoustic transducer included in sensors 96 or other alert signal perceptible by the patient or transmitted and received by an external device such as device 40 of FIG. 1.

User-programmable sensing and therapy delivery control parameters may be programmed into memory 82 via telemetry circuitry 88. Telemetry circuitry 88 includes a transceiver and antenna for communicating with external device 40 (shown in FIG. 1) using RF communication. Telemetry circuitry 88 may receive downlink telemetry from and send uplink telemetry to external device 40.

ECG episode data related to saturation events and lead issue detection may be stored in memory 82 and transmitted by telemetry circuitry 88 to external device 40 upon receipt of an interrogation command. Clinician or technician review of ECG episodes that include saturation events facilitates proper diagnosis of a lead issue, enabling corrective action to be taken, such as reprogramming ICD 14 to use different therapy and/or sensing vectors, replacement of lead 16, or adjustment of the connection between lead 16 and ICD 14.

Figure 3:
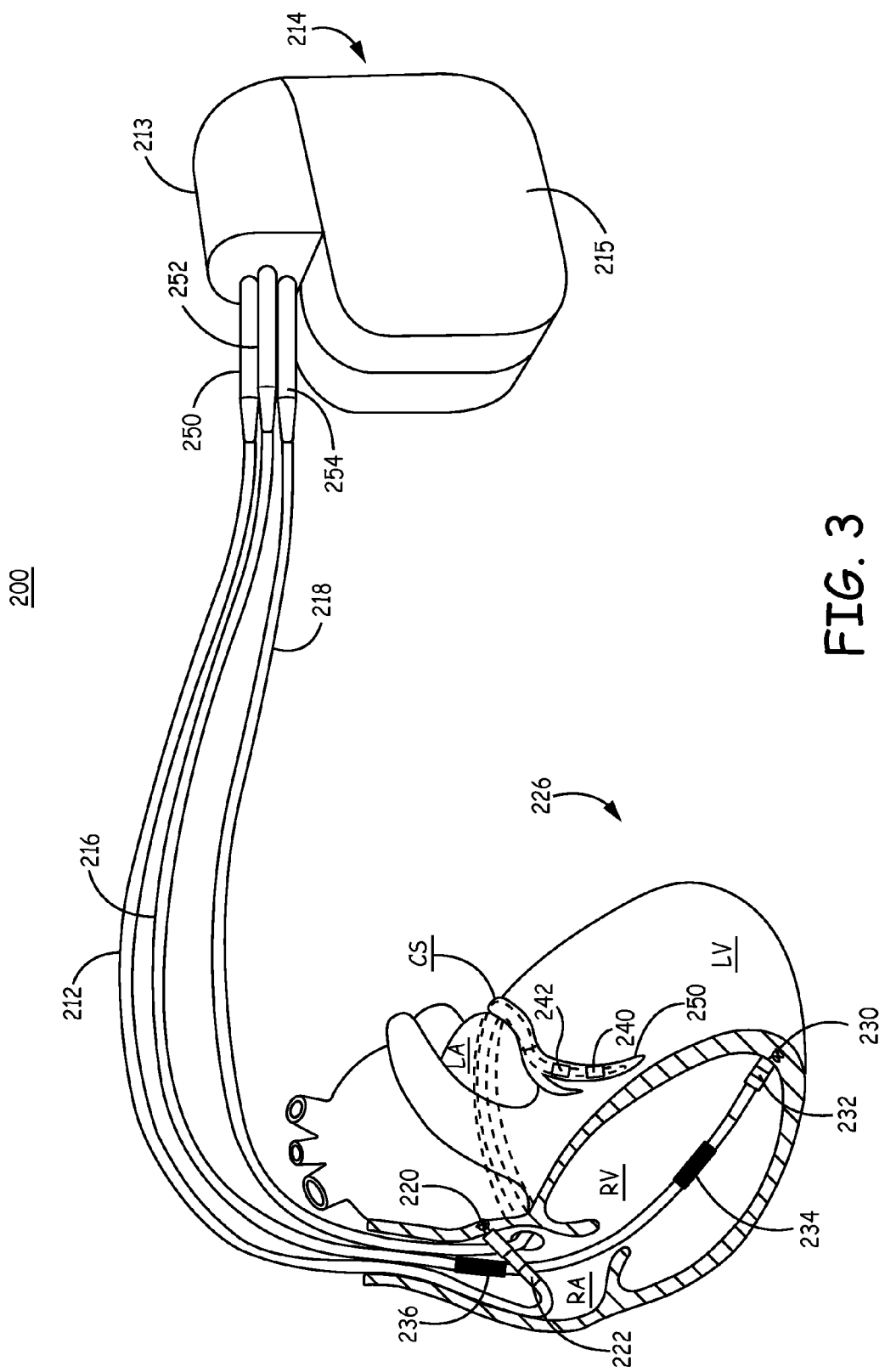
FIG. 3 is a schematic representation of an IMD system that includes an ICD and transvenous leads and is capable of delivering high voltage and low voltage therapies to a patient's heart.

FIG. 3 is a schematic representation of an IMD system 200 that includes an ICD 214 capable of delivering high voltage and low voltage therapies to heart 226. The presently disclosed techniques for detecting saturation events and controlling shock delivery in response to saturation event detection may be implemented in an IMD system 200 that includes transvenous lead(s) that extend into heart 226.

ICD 214 is coupled to heart 226 via leads 212, 216, and 218. Right atrial lead 212 extends from ICD 214 to the right atrium (RA) and carries distal electrodes 220 and 222 for sensing cardiac electrical signals and delivering pacing pulses in the RA. In addition, ICD housing 215 may be used as a return electrode in combination with electrodes 220 and/or 222 to deliver the pacing pulses in the RA.

Right ventricular lead 216 carries a tip electrode 230 and a ring electrode 232 for sensing cardiac electrical signals and delivering pacing pulses in the RV. RV lead 216 may additionally carry high voltage electrodes 234 and 236, referred to herein as the RV defibrillation electrode 234 and the superior vena cava (SVC) defibrillation electrode 236, for delivering high voltage cardioversion and defibrillation shocks in response to detecting a shockable VT from sensed cardiac signals. Housing 215 may be used with pace/sense electrodes 230 and 232 for delivering RV pacing pulses or in combination with defibrillation electrodes 234 and/or 236 during shock delivery.

A coronary sinus (CS) lead 218 is shown extending into a cardiac vein 250 via the RA and coronary sinus for positioning electrodes 240 and 242 for sensing cardiac signals and delivering pacing pulses along the left ventricle (LV). In some examples, CS lead 18 may additionally carry electrodes for positioning along the left atrium (LA) for sensing and stimulation along the left atrial chamber. CS lead 218 may carry additional electrodes positioned along the left ventricle, e.g., four electrodes or more for providing multiple selectable pacing or sensing vectors. Housing 215 may be used as an electrode in combination with electrodes 240 and/or 242 to deliver the pacing pulses to the LV.

The depicted positions of leads 212, 216 and 218 in or about the right and left heart chambers are merely illustrative. Other leads and pace/sense electrodes and/or high voltage CV/DF electrodes can be used instead of, or in combination with, any one or more of the depicted leads and electrodes shown in FIG. 3. ICD 214 is shown as a multi-chamber device capable of sensing and stimulation in three or all four heart chambers. It is understood that ICD 214 may be modified to operate as a single chamber device, e.g., with a lead positioned in the RV only, or a dual chamber device, e.g., with a lead positioned in the RA and a lead positioned in the RV.

In general, ICD 214 may be embodied as any single, dual or multi-chamber device configured to receive at least one medical electrical lead by a connector assembly 213 having one or more bores for mating with a respective number of lead connectors. Electrodes carried by a lead coupled to ICD 214 are used for sensing cardiac electrical signals and for delivering shock therapy to heart 226. ICD 214 may be embodied as an ICD capable of delivering both low voltage pacing pulses, e.g., for bradycardia pacing, anti-tachycardia pacing, etc., and high voltage CV/DF shocks.

Each of leads 212, 216 and 218 include insulated electrical conductors extending from the respective electrodes 220, 222, 230, 232, 234, 236, 240 and 242 to a respective proximal connector 250, 252, or 254 that electrically couples the electrodes to circuitry enclosed by housing 215 when the proximal connectors 250, 252 and 254 are properly positioned in IMD connector assembly 213. Circuitry enclosed in housing 215 may generally correspond to the modules and their associated functions shown and described in conjunction with FIG. 2 above. Instead of electrodes 24, 28 and 30 as shown in FIG. 2, electrodes 220, 222, 230, 232, 234, 236, 240 and 242 may be selectively coupled to electrical sensing circuitry 86 via switching circuitry in which case sensing circuitry 86 may include multiple sensing channels, e.g., a RA sensing channel, RV sensing channel and LV sensing channel. Electrodes 220, 222, 230, 232, 234, 236, 240 and 242 may be coupled to therapy delivery circuitry 84 for delivering low voltage pacing pulses for bradycardia pacing or anti-tachycardia pacing to the respective heart chambers or for delivering shock therapy.

Sensing circuitry 86 in FIG. 2 may be controlled by control module 80 to sense a near-field EGM signal and a far-field EGM signal as generally disclosed in U.S. Pat. No. 8,078,277 (Gunderson, et al.), incorporated herein by reference in its entirety. The far-field EGM signal may be analyzed at the time that the electrical sensing circuitry 86 senses a cardiac event to identify if oversensing of noise in the near-field EGM is occurring. Control module 80 may compare an amplitude of the far-field EGM signal at a time substantially coincident with the time of a sensed cardiac event to a threshold amplitude. The threshold amplitude may correspond to a very low baseline, such as an isoelectric baseline, of the far-field EGM. The far-field EGM may exhibit a flat isoelectric baseline during oversensing of noise on the near-field EGM signal. False detection of VT due to oversensing of noise may be avoided by identifying noise in the near-field EGM signal through the analysis of the far-field EGM signal.

After a shock is delivered, however, the baseline of the far-field EGM signal may be disturbed such that analysis of the far-field EGM signal may not reliably reject near-field EGM signal noise after shock delivery during VT redetection algorithms. As a result, a shock may be redelivered due to a lead-related issue causing noise on the near-field EGM signal that is oversensed when the far-field EGM baseline is disturbed and unavailable for noise rejection analysis.

In order to reject noise on the near-field signal, the control module 80 may detect saturation events of the near-field EGM signal and store a time and date stamp of each saturation event and/or track saturation events using counters. If VT is detected, control module 80 analyzes the logged saturation events and withholds shock delivery if the logged saturation events satisfy lead issue criteria, indicating the detected VT is likely a false VT due to oversensing of electrical noise potentially caused by a lead issue.

Figure 4:
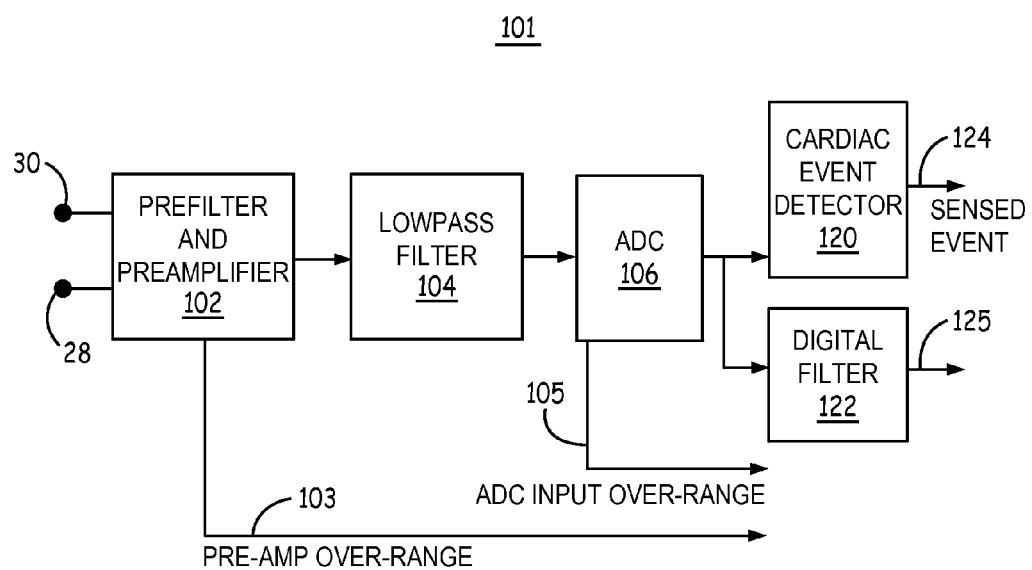
FIG. 4 is a block diagram of an example sensing channel of the sensing circuitry of FIG. 2.

FIG. 4 is a block diagram of an example sensing channel 101 of sensing circuitry 86 of FIG. 2. The sensing channel 101 may receive an electrical signal developed across input electrodes coupled to sensing channel 101, e.g., electrodes 28 and 30 of FIG. 1 or any of the electrodes coupled to ICD 214 shown in FIG. 3. Sensing channel 101 is shown coupled to electrodes 28 and 30 in this example, but other electrodes or other combinations of available electrodes may be coupled to sensing channel 101. Sensing circuitry 86 may include multiple sensing channels similar to sensing channel 101 for each sensing vector signal to be analyzed for use in detecting VT. In the case of multiple sensing channels, sensing circuitry 86 may include duplicate components for each sensing channel 101, or the sensing channels may share one or more components.

In this example, sensing channel 101 includes a pre-filter and pre-amplifier 102, low-pass filter 104, analog-to-digital converter (ADC) 106, cardiac event detector 120 and digital filter 122. The configuration of sensing channel 101 is illustrative in nature and should not be considered limiting of the techniques described herein. The sensing channel 101 of sensing circuitry 86 may include more or fewer components than illustrated and described in FIG. 4.

The electrical signal developed across input electrodes 28 and 30 is provided as a differential input signal to pre-filter and pre-amplifier 102. Non-physiological high frequency and DC signals may be filtered by a wideband bandpass filter included in pre-filter and pre-amplifier 102, and high voltage signals may be removed by protection diodes included in pre-filter and pre-amplifier 102. Pre-filter and pre-amplifier 102 amplifies the pre-filtered signal by a gain and may convert the differential signal to a single-ended output signal passed to low pass filter 104.

Pre-filter and pre-amplifier 102 may, in some examples, generate a pre-amp over-range signal 103 when the pre-filtered signal exceeds a range of the pre-amplifier input. For example, an amplifier included in pre-filter and pre-amplifier 102 may have an input range of approximately ±10 to 20 millivolts (mV), however, the input range may be smaller or larger in other examples. Pre-filter and pre-amplifier 102 may generate the pre-amp over-range signal 103 when the input signal causes the preamplifier to be over-range. Such a condition may be evidence of a saturation event due to a lead-related issue. The pre-amp over-range signal 103 may be provided to control module 80 for detecting saturation events.

The pre-amplified signal output of pre-filter and pre-amplifier 102 is passed to low pass filter 104. Low pass filter 104 may provide anti-alias filtering and noise reduction prior to digitization. The filtered signal output of low pass filter 104 is passed to ADC 106, which converts the analog signal to a digital bit stream. In one example, ADC 106 may be a sigma-delta converter (SDC), but other types of ADCs may be used. ADC 106 may include a decimator, which functions as a digital low-pass filter that increases the resolution and reduces the sampling rate. In one example, ADC 106 may have an 8-bit resolution and 16 kiloHertz (kHz) sampling rate and include a decimator having a 16-bit resolution and a 1 kHz sampling rate. These values are intended for illustrative purposes only and should not be considered limiting of the techniques described herein.

ADC 106 may have other characteristics, such as an input range and a slew rate range. In one example, the input amplitude range of ADC 106 may be between 25 and 825 mV and the slew rate range may be from 0 to 6.24 mV/ms, 3.12 mV/ms, 1.56 mV/ms, or 0.78 mV/ms. ADC 106 may be configured to generate an ADC input over-range signal 105 when the input signal amplitude is greater than the input amplitude range of ADC 106. Such a condition may be evidence of a saturation event caused by electrical noise due to a lead issue. The ADC input over-range signal 105 may be provided to control module 80 for detecting saturation events and controlling shock delivery.

The digitized signal output from decimator 108 may be provided to the cardiac event detector 120 and the ECG digital filter 122. Cardiac event detector 120 may include a bandpass filter (e.g., 10 to 32 Hz), rectifier, and threshold crossing detector. The cardiac event detector 120 may, in one example, operate by setting an auto-adjusting sensing threshold that dynamically varies from a percentage of the peak value of the currently detected cardiac event signal, e.g., the peak amplitude of a sensed R-wave, and a programmed minimum value according to one or more decay rates or step drops. A sensed event signal 124 is output from cardiac event detector 120 and passed to control module 80 to indicate that a cardiac event is detected, e.g., an R-wave or P-wave, when the received electrical signal exceeds the cardiac event sensing threshold.

In some examples, control module 80 is configured to perform signal morphology analysis of the cardiac electrical signal. In this case, digital filter 122 may apply a bandpass filter (e.g., with a bandwidth of 2.5 to 32 Hz) to provide a filtered, digitized cardiac signal 125 to control module 80 for performing morphology analysis according to implemented VT detection algorithms.

Control module 80 may detect saturation events in response to pre-amp over-range signal 103 and/or ADC input over-range signal 105 and/or by analysis of the digital cardiac signal 125 received from digital filter 122. In one example, if cardiac signal 125 reaches or exceeds a saturation amplitude threshold, in either the positive or negative direction, for a predetermined time interval or threshold number of sample points, control module 80 detects a saturation event. As used herein, a "saturation event" is an event that meets saturation criteria that include at least reaching either a maximum or a minimum saturation amplitude threshold, which may or may not be equal to the maximum and minimum input range, respectively, of componentry of sensing channel 101. In some examples, the positive and negative saturation amplitude thresholds may be defined as amplitudes that are less than the saturation amplitude input range of sensing channel 101. For example, ADC 106 may have in input range of ±8 mV and the saturation amplitude threshold may be defined as ±8 mV, equal to the input range in this example. In another example, however, the ADC input range may be ±16 mV, but the saturation amplitude threshold may be programmed to be less than ±16 mV, e.g., ±8 mV or any programmed value of ±6 mV to ±10 mV, with no limitation intended.

Control module 80 may detect the saturation event in response to the pre-amp over-range signal 103 or the ADC input over-range signal 105 being present for a predetermined time interval. Additionally or alternatively, a saturation event may be detected in response to digital signal 125 reaching a saturation amplitude threshold for a required number of sample points. Both the polarity (positive or negative) and the time and date stamp of a saturation event may be stored in memory 82 by control module 80 when a saturation event is detected. The total number of sample points at or above the saturation amplitude threshold for each saturation event may also be stored for use in determining irregularity of the duration of saturation events as described below in conjunction with FIG. 6.

The sensing channel 101 illustrated in FIG. 4 is one example of a sensing channel that may be implemented in conjunction with the techniques disclosed herein. Other configurations of a sensing channel or arrangement of components in the sensing channel may be utilized.

Figure 5:
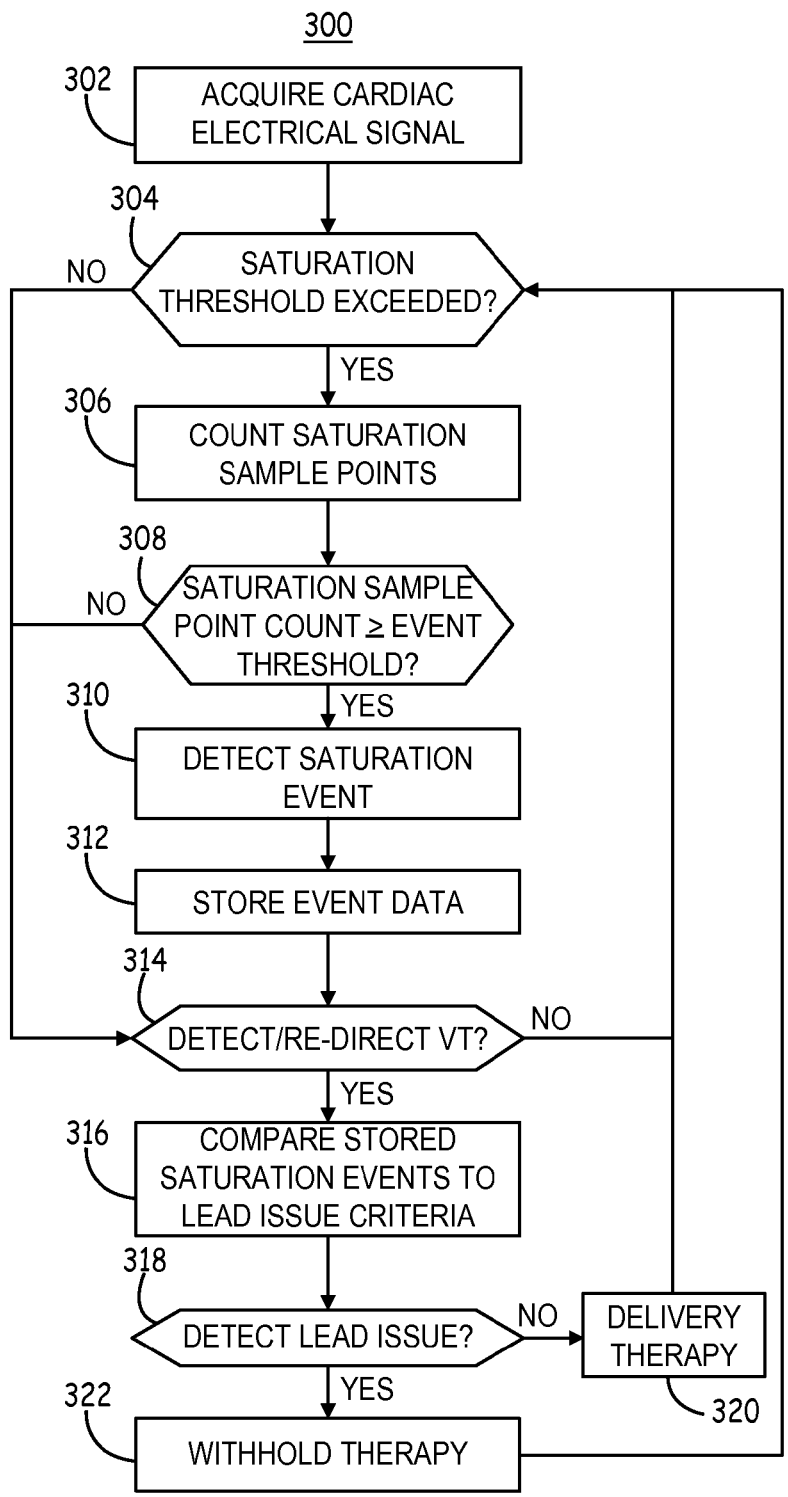
FIG. 5 is a flow chart of one method for controlling shock therapy delivered by an ICD according to one example.

FIG. 5 is a flow chart 300 of one method for controlling shock therapy delivered by an ICD according to one example. The process shown by flow chart 300 may be implemented in the ICD 214 shown in FIG. 4 or in the ICD 14 shown in FIG. 1. At block 302, control module 80 receives the digitized cardiac electrical signal 125 (e.g., ECG or EGM signal) from sensing circuitry 86. At block 304, control module 80 determines if the received signal exceeds the saturation amplitude threshold. In some examples, control module 80 may determine that the received signal exceeds the saturation amplitude threshold when an over-range signal 103 and/or 105 is received from sensing circuitry 86 at block 304. If control module 80 determines that the received signal exceeds the saturation amplitude threshold, e.g., an over-range signal 103 or 105 is received at block 304, control module 80 may begin to count consecutive saturation sample points of the digitized signal 125 at block 306. Saturation sample points may be counted as long as the received signal exceeds the saturation amplitude threshold, e.g., as long as the over-range signal 103 or 105 is present.

In other examples, saturation sample points are identified by control module 80 after receiving an over-range signal 103 or 105 by comparing subsequent sample points to a maximum saturation amplitude threshold, e.g., ±8 mV, and to a minimum saturation amplitude threshold, e.g., −8 mV. In still other examples, the over-range signals 103 and 105 may not be required in order to detect a saturation event. When lead issue detection based on saturation events is enabled, control module 80 may compare sample points of cardiac electrical signal 125 to the positive and negative saturation amplitude thresholds (e.g., the positive and negative input range limits of ADC 106 or a selected amplitude less than the input range limits) and count consecutive sample points of the same polarity that are at least equal to or exceed the saturation amplitude threshold. Control module 80 may be configured to search for a peak amplitude after receiving a cardiac sensed event signal 124 and if the peak amplitude of the cardiac electrical signal 125 reaches the saturation amplitude threshold, begins counting consecutive saturation sample points, e.g., by counting sample points equal to or exceeding the saturation amplitude threshold having the same polarity.

In some cases, a noise signal may occur first in a positive or negative direction then switch to the opposite polarity in the opposite direction. The rectified cardiac signal used by cardiac event detector 120 may sense a single cardiac event due to blanking and refractory periods. Control module 80, however, may be configured to count consecutive sample points having the same polarity and exceeding the saturation amplitude threshold in the first direction then start counting the next consecutive sample points having the opposite polarity and exceeding the opposite saturation amplitude threshold such that two saturation events of opposite polarity may be detected, even if the two saturation events are oversensed as a single cardiac event by cardiac event detector 120.

Consecutive sample points having the same polarity at or exceeding the saturation threshold limit are counted at block 306. If the consecutively counted sample points (all of the same polarity) exceeding either the positive or negative saturation threshold reach a saturation event threshold at block 308, a saturation event is detected at block 310. The saturation event threshold applied at block 308 may be as low as a single sample point, e.g., a count of one, but may be required to be multiple consecutive sample points in other examples, e.g., at least two consecutive sample points. The saturation event threshold may be thought of as a saturation duration threshold since it is a requirement relating to how long the cardiac signal 125 equals or exceeds the saturation amplitude threshold without dropping below the threshold amplitude.

The techniques described above for detecting a saturation event may be modified in other examples and the methods disclosed herein are not limited to a particular method for detecting saturation events. Methods used will depend in part on the particular hardware implemented in sensing channel 101 and the signals received by control module 80.

Generally, a cardiac electrical signal received by sensing channel 101 that exceeds a predetermined saturation amplitude threshold, for a predetermined time interval may be detected as a saturation event. The saturation amplitude threshold may be based in part on the input range of the sensing channel 101 but is not limited to a maximum or minimum input range. The saturation amplitude threshold may be defined as the maximum and minimum input range limits of any component of sensing channel 101 or within a threshold range of the maximum and minimum input range limits, e.g., within approximately 50% or more of the input range limits.

When a saturation event is detected at block 310, saturation event data is stored at block 312. For example, the polarity of the event, the duration or number of sample points meeting or exceeding the saturation amplitude threshold, along with a time stamp (which may include time and date) may be stored at block 312. In some examples, a segment of the cardiac electrical signal including the detected saturation event is stored in memory 82 for availability for clinician or technician review.

Additionally or alternatively, control module 80 may increase saturation event counters at block 312. A positive saturation event counter may be increased when a positive saturation event is detected and a negative saturation event counter may be increased when a negative saturation event is detected. In some cases, positive and negative saturation event counts may be updated for the most recent n sensed cardiac events, e.g., the most recent 12 RR intervals or other predetermined number of RR intervals, such that when a VT detection is made by control module 80 the number and polarity of saturation events occurring within the most recent n sensed events is known.

Control module 80 performs, at block 314, implemented VT detection algorithms using the cardiac electrical signal 125 and/or cardiac sensed event signals 124 received from at least the sensing channel 101 from which saturation events were detected and may use signals from one or more other sensing channels for detecting or re-detecting VT. If VT is detected at block 314, control module 80 compares stored saturation event data to lead issue detection criteria at block 316. Lead issue detection criteria may include, for example, near-term saturation event criteria, relatively longer-term saturation event criteria, and/or event irregularity criteria. One example criteria for detecting a lead issue due to saturation events is described in conjunction with the flow chart 400 of FIG. 6.

If lead issue detection criteria are not satisfied, as determined at block 318, a therapy is delivered at block 320 in accordance with programmed therapy delivery control parameters in response to the VT detection Delivered therapy may include ATP and/or high voltage shock delivery. If a lead issue is detected at block 318 due to saturation events, therapy for terminating the detected VT is withheld at block 322. The process returns to block 304 to continue monitoring for saturation events. Saturation events may be detected from the received cardiac electrical signal after delivery of a shock (or ATP) at block 320, during VT redetection. As such, the VT detection made at block 314 may be a re-detection of VT after therapy is delivered in response to an initial detection of a VT episode. A lead issue may be detected at block 318 based on saturation events detected after (and, in some cases saturation events detected before) therapy delivery within predetermined near-term and long-term time intervals at block 314 and cause a shock to be withheld at block 322 following VT redetection.

Figure 6:
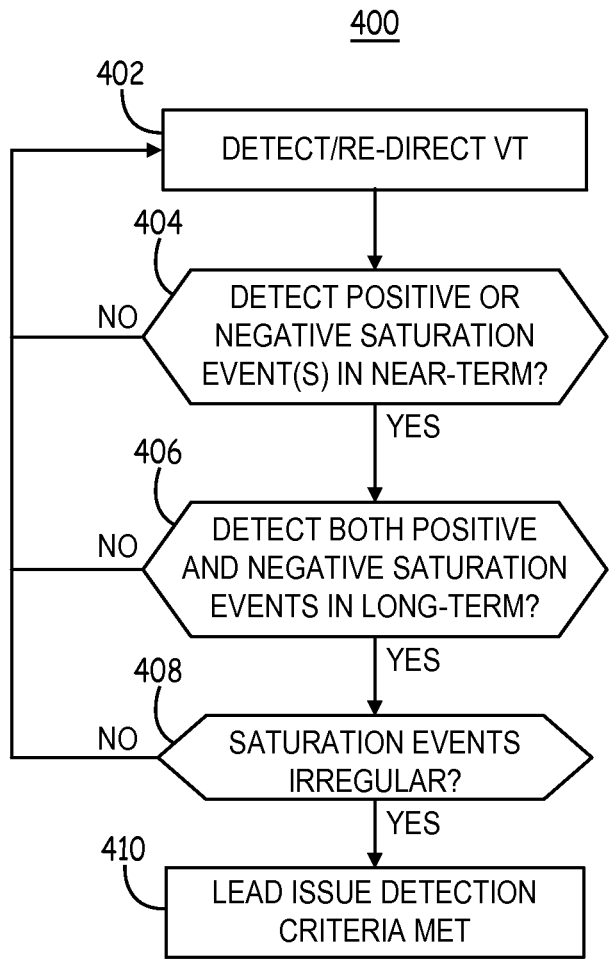
FIG. 6 is a flow chart of a method for detecting a lead issue based on detected saturation events according to one example.

FIG. 6 is a flow chart 400 of a method for detecting a lead issue based on detected saturation events according to one example. Combinations of one or more of the comparisons made in the flow chart 400 at block 404, 406 and 408 may be performed at block 316 of FIG. 5 for detecting a lead issue. Upon detecting or re-detecting a VT at block 402 (which may correspond to block 314 of FIG. 5), control module 80 may determine if at least one saturation event of positive or negative polarity has occurred in a near-term time interval at block 404. The near-term time interval may include at least a portion of a time interval over which the cardiac electrical signal (from which saturation events are detected) is analyzed by control module 80 for detecting the VT. The near-term time interval may end at the time point that the VT detection is made at block 402.

The near-term time interval may be defined as a number of most recent cardiac event intervals, e.g., RR intervals based on R-wave sensed event signals received from cardiac event detector 120. In one example, control module 80 determines if a saturation event, either positive or negative, has occurred within the last 12 RR intervals. In other examples, control module 80 determines if at least one saturation event, either positive or negative, has occurred within the last m RR intervals, where m corresponds to the n out of m cardiac event intervals shorter than a tachyarrhythmia detection interval required to detect (or redetect) the VT. For example, if 12 out of 18 RR intervals are required to be tachyarrhythmia detection intervals (e.g., shorter than 320 ms), control module 80 may determine if at least one saturation event occurred during the most recent 18 RR intervals.

In some examples, a single saturation event of either positive or negative polarity may be required to fulfill the near-term saturation event criteria for detecting a lead issue. In other examples, more than one saturation event within the predefined near-term time interval may be required to satisfy the near-term saturation event criteria. If the near-term saturation event criteria are not satisfied, a lead issue is not detected. A shock (or ATP) therapy may be delivered in response to the VT detection (or re-detection) and control module 80 returns to block 402 until VT is detected again.

If the near-term saturation event criteria are satisfied at block 404 or the lead issue detection criteria does not include a near-term saturation event criteria, control module 80 determines if detected saturation events satisfy long-term event criteria for detecting a lead issue at block 406. In one example, at least one positive saturation event detection and at least one negative saturation event detection within the predefined long-term time interval are required in order to detect a lead issue. The long-term time interval, which may be defined as a time interval or number of cardiac cycles, is longer than the near-term time interval and may extend earlier in time from the time point that the VT is detected at block 402 than the near-term time interval. The long-term time interval may be one minute, two minutes, five minutes, ten minutes or other predefined time period that ends upon VT detection or ends upon the onset of the near-term time interval.

If the long-term saturation event criteria are not satisfied, e.g., at least one positive saturation event detection and at least one negative saturation event detection is not detected within the predefined long-term time interval, a lead issue is not detected. A shock (or ATP) therapy may be delivered in response to the VT detection (or re-detection) and control module 80 returns to block 402 until VT is detected again.

If at least one positive and one negative saturation event are detected within the long-term time interval at block 406 or the lead issue detection criteria does not include a near-term saturation event criteria, control module 80 may determine the irregularity of the detected saturation events over the near-term, over the long-term or both in block 408. Irregularity of the detected saturation events may be determined based on the polarity of the detected saturation events and/or the duration of the saturation events. For example, if more than one saturation event occurs in the near-term and all saturation events during the near term have the same polarity, the saturation events may be determined to be regular and the irregularity criterion are not satisfied. If the irregularity criteria at block 408 are not satisfied a schedule shock (or ATP) is delivered and control module 80 returns to block 402 until VT is detected again. The irregularity criteria may, in one example, only be satisfied if at least two different polarities of saturation events have occurred when more than one saturation event is detected in the near term.

Saturation events of all the same polarity may be high amplitude VT R-waves. In this case, the VT detection and subsequent therapy is appropriate. The irregularity criteria may require that less than a maximum number of consecutive saturation events be of the same polarity, e.g., if more than three consecutive saturation events of the same polarity occur, the events are not determined to be irregular at block 408.

In some cases, the high amplitude VT R-waves occur at regular intervals, e.g., during monomorphic VT. As such, irregularity criteria applied at block 408 may include a requirement of irregular event intervals that end on detected saturation events. Intervals between each saturation event and the immediately preceding detected event, either a cardiac sensed event signal or preceding saturation event, may be compared to a running RR interval average or other metric of the currently detected heart rate to verify that the interval ending on the saturation event is outside a predetermined range of the currently detected heart rate interval.

In another example, irregularity in saturation event duration, e.g., determined as the coefficient of variation in the number of sample points counted for each detected saturation event, may be used to detect irregularity at block 408. Large amplitude R-waves during VT are expected to have a more regular duration, or signal width, at the saturation amplitude threshold than saturation events caused by a lead issue. Accordingly, in some examples, control module determines the coefficient of variation of the duration of the saturation events or other metric of the variation of the duration of the saturation events detected during the near-term interval, long-term interval or both. The duration of each saturation event may be determined as the sample point counts at or exceeding the saturation amplitude threshold. The coefficient of variation or other duration variation metric may be compared to an irregularity threshold at block 408 to determine if irregularity criteria are met.

As such, irregularity criteria may be applied to the polarity, saturation event time intervals, and/or saturation event duration to exclude high amplitude VT from being falsely detected as a lead issue. By requiring both positive and negative saturation events in at least the long-term (and/or the near-term), false lead issue detection due to high amplitude VT R-waves may be avoided without additional irregularity criteria since high amplitude R-waves are expected to all have the same polarity. However, additional criteria that require irregularity in the polarity and/or saturation event duration, for example, may be applied at block 408 to reduce the likelihood of falsely detecting a lead issue due to high amplitude VT R-waves.

If the near-term criteria, long-term criteria and irregularity criteria are satisfied, lead issue detection criteria are met at block 410. In other examples, only one of the near-term criteria, long-term criteria and irregularity criteria need to be satisfied. In yet other examples only two of the criteria need to be satisfied, e.g., only the near-term and long-term criteria are required to be satisfied in order to detect a lead issue, or only one of the near-term criteria and the irregularity criteria or only the long-term criteria and the irregularity criteria. Referring again to FIG. 5, a lead issue detection is made at block 318 when the detection criteria are met. A scheduled VT therapy is withheld at block 322 in response to the lead issue detection as described above in conjunction with FIG. 5.

Figure 7:
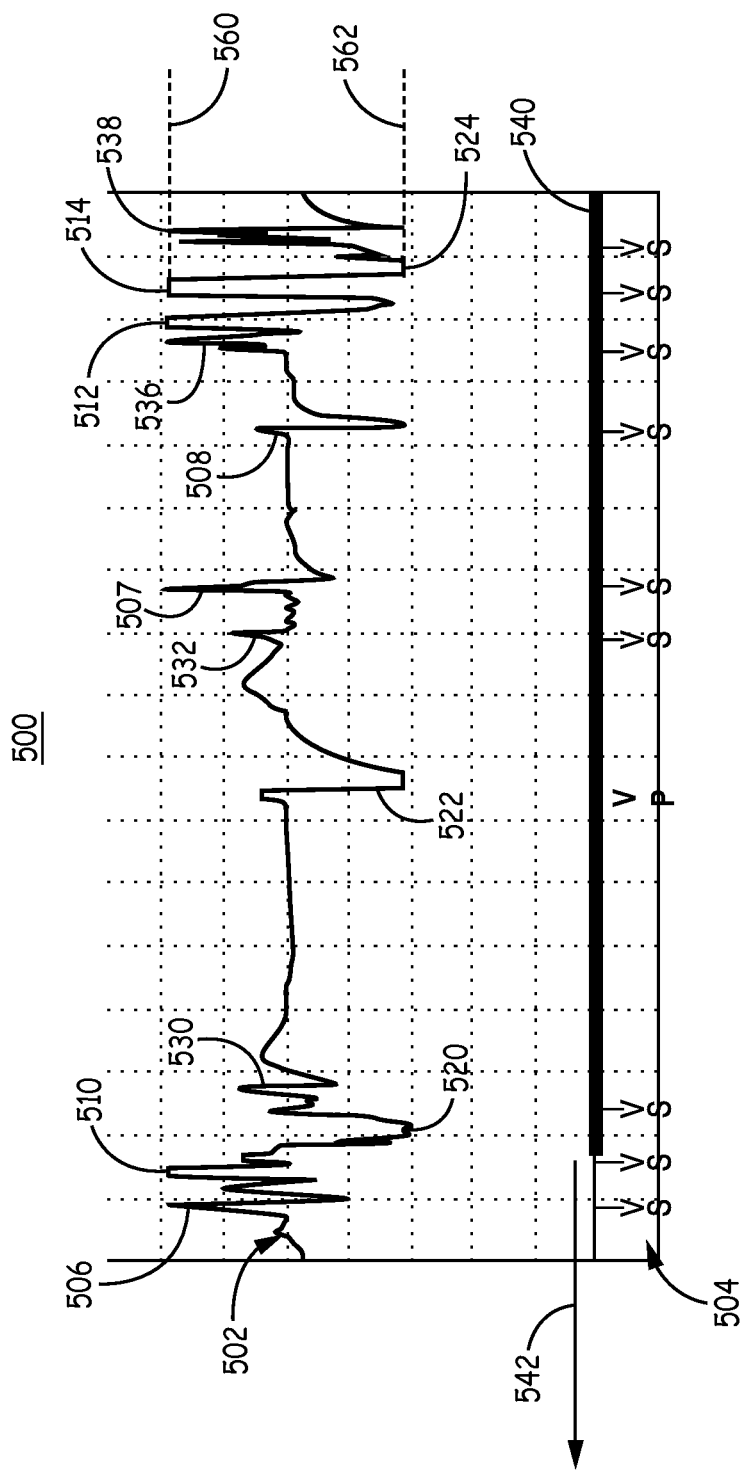
FIG. 7 is a sample recording of a cardiac electrical signal including saturation events.

FIG. 7 is a sample recording of a cardiac electrical signal 502 including saturation events. Cardiac electrical signal 502 includes valid R-waves 506, 507 and 508 that are appropriately sensed, as indicated by R-wave sensed event signals (VS) shown on marker channel 504. Noise signals 510, 512, 514, 520, 524, 530 and 532 are also each sensed as R-waves as indicated by VS markers on marker channel 504. A ventricular pacing pulse 522 is denoted by VP on the marker channel 504. Noise signals 510, 512 and 514 are detected by control module 80 as positive polarity saturation events because the signal amplitude is at the maximum saturation amplitude threshold 560 for a predetermined number of consecutive sample points. Noise signals 520 and 524 are detected as negative saturation events because the signal amplitude is at the minimum saturation amplitude threshold 562 for a predetermined number of consecutive sample points meeting the saturation event detection criteria.

Other noise signals 530 and 532 are falsely detected as R-waves as indicated by VS markers but may not reach the saturation event detection criteria (based on not reaching the maximum or minimum saturation amplitude thresholds 560 or 562 and/or not reaching the required number of consecutive sample points at or exceeding the maximum or minimum saturation amplitude thresholds). In some examples, the R-wave sense event signals produced in response to noise signals 530 and 532 may be identified as oversensed events by control module 80 and contribute to detecting a lead integrity alert condition. As described below, when a lead integrity alert condition is detected based on oversensing criteria and/or lead impedance measurements, monitoring of saturation events for controlling VT therapy is enabled.

If a VT detection is made based on VS events, saturation events occurring in a near-term time interval 540, which may correspond to the most recent 10 VS events in this example, are compared to near-term lead issue detection criteria. Since at least one saturation event has occurred in the near-term, the near term detection criteria are satisfied. Control module 80 may compare saturation events occurring in a long-term time interval 542 that may extend several minutes earlier than the VT detection (and may or may not include near-term time interval 540). If at least one positive saturation event and at least one negative saturation event occur, the long-term lead detection criteria are satisfied. Control module 80 detects a lead issue event based on the positive saturation events 510, 512 and 514 and negative saturation events 520 and 524 occurring within the near- and long-term time intervals 540 and 542 in this example.

Control module 80 may additionally require that the saturation events 510, 512, 514, 520 and 524 have irregular saturation durations and/or do not exceed a maximum limit of consecutive saturation events of the same polarity. When the lead issue criteria are satisfied, a therapy is withheld in response to a VT detection.

Figure 8:
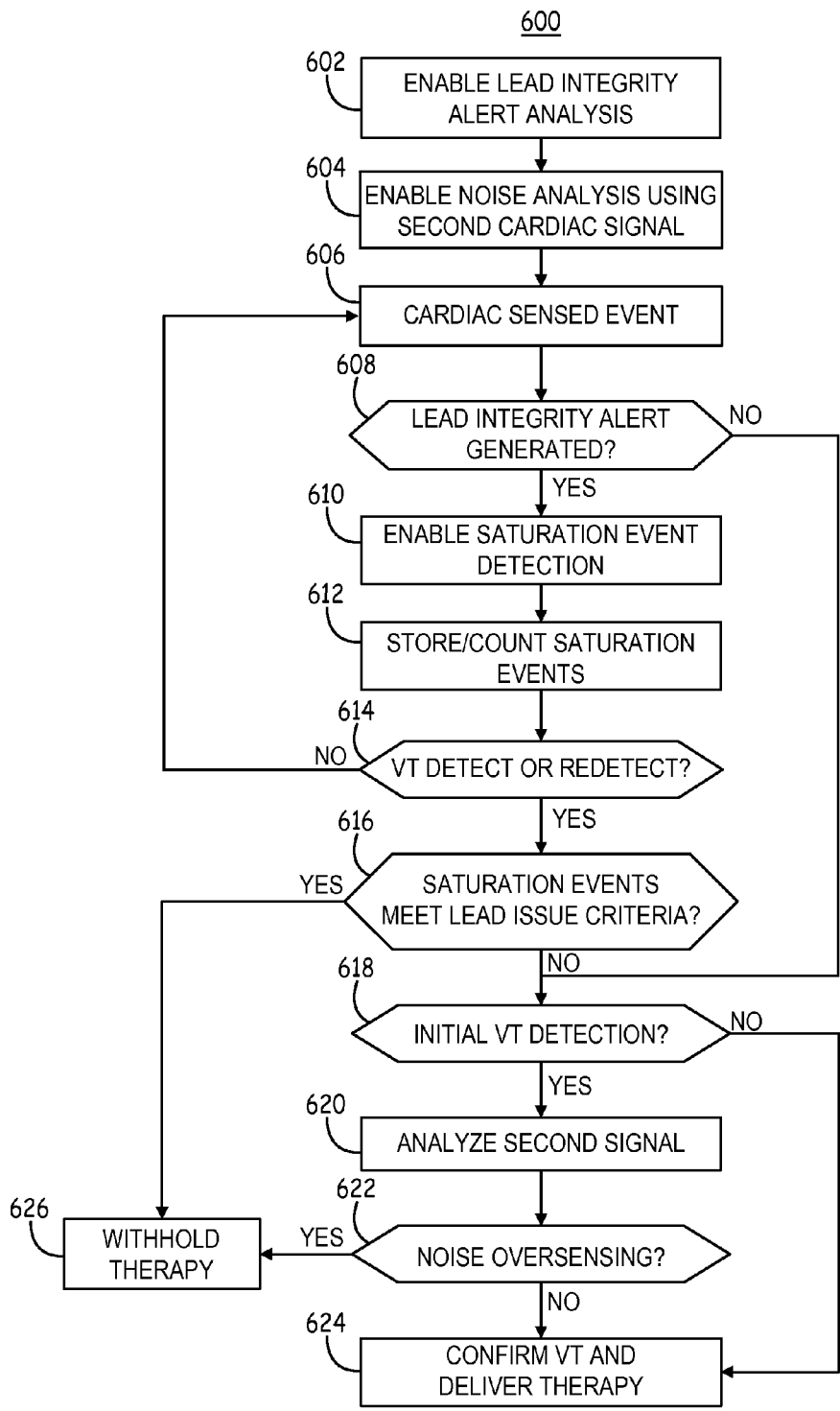
FIG. 8 is a flow chart of a method for controlling therapy based on lead issue monitoring according to one example.

FIG. 8 is a flow chart 600 of a method for controlling therapy based on lead issue monitoring according to one example. At block 602, a lead integrity alert analysis is enabled. Control module 80 may be configured to analyze a cardiac electrical signal of oversensing conditions and measure lead impedances for identifying lead conditions and generating an alert. The lead integrity alert analysis may be performed by ICD 14 or ICD 214 according to methods generally disclosed in U.S. Pat. No. 7,289,851 (Gunderson et al.), which is incorporated herein by reference in its entirety. The lead integrity alert analysis is performed to identify lead conditions that may lead to false VT detection and for generating an alert when the lead condition when oversensing criteria and/or lead impedance criteria are met.

At block 604, noise analysis using a second cardiac signal is enabled. In some examples, when VT is detected, noise analysis may be performed using a second cardiac signal, different than a cardiac signal from which sensed events led to a VT detection. For example, in IMD system 200 of FIG. 3, ICD 214 may be configured to sense R-waves from a near-field EGM signal using RV electrodes 230 and 234. If a required number of tachyarrhythmia intervals to detect VT (NID) is reached in response to R-wave sensed event signals from the RV sensing channel of sensing circuitry 86, a second EGM signal may be evaluated to determine if sensed R-waves were likely to be noise or valid R-waves. The second EGM signal is received using a different pair of electrodes than the first, near-field EGM signal. The second EGM signal may be a far-field EGM signal, e.g., an EGM signal acquired using a coil electrode 234 or 236 and housing 215.

The far-field EGM signal includes true R-waves but is expected to have a relatively flat baseline between R-waves. If events sensed from the near-field EGM signal occur during a relatively flat baseline portion of the far-field EGM signal, oversensing of noise on the near-field EGM signal, possibly due to a lead issue, may be occurring. If events occur substantially simultaneously on both the near-field signal and the far-field signal, the VT detection is confirmed. If analysis of the far-field EGM signal reveals a relatively flat baseline at times when R-wave sense event signals are produced by sensing channel 101 receiving the near-field EGM signal, the VT detection is likely due to noise oversensing. The use of a second signal for identifying oversensing of cardiac events is generally disclosed in the above-incorporated U.S. Pat. No. 8,078,277 (Gunderson, et al).

A second cardiac electrical signal may also be used for identifying VT detections likely due to noise oversensing in the IMD system 10 of FIG. 1. If a VT NID or other VT detection criteria are reached using an ECG signal sensed between sensing electrodes 28 and 30, for example, a second ECG signal, e.g., between defibrillation electrode 24 and housing 15 may be analyzed as described above to determine if a relatively flat baseline signal of the second ECG signal indicates oversensing of noise in the first ECG signal.

When a cardiac event is sensed, as indicated at block 606, control module 80 may determine if the sensed event triggers a lead integrity alert to be generated as generally disclosed in the above-incorporated '851 patent. If a lead integrity alert condition is not detected and an alert is not generated, the process advances to block 618. Detection of saturation events is not enabled. If the sensed cardiac event results in an initial VT detection, as determined at block 618, e.g., based on a VT NID being reached or other VT detection criteria, a second cardiac electrical signal is analyzed at block 620 according to the enabled noise analysis feature for detecting oversensing of cardiac events. The noise analysis may be performed before, during and/or after capacitor charging in preparation for shock delivery is completed in response to the VT detection made at block 618. The noise analysis may be performed according to the techniques disclosed in the above-incorporated '277 patent.

If noise oversensing is identified in the first cardiac electrical signal at block 622 based on the analysis of the second cardiac electrical signal performed at block 620, the VT detection is determined to be due to noise oversensing. A scheduled therapy for terminating the detected VT is withheld at block 626. If noise oversensing is not identified, the detected VT is confirmed, and therapy is delivered to terminate the VT according to programmed therapy delivery protocols at block 624.

When the VT detection is not an initial detection as determined at block 618, e.g., when VT is being redetected after therapy has been delivered following an initial VT detection of the tachyarrhythmia episode, the noise analysis using a second cardiac signal is not performed. Therapy delivery, e.g., delivery of a CV/DF shock, may disturb the isoelectric baseline signal of the second cardiac electrical signal such that verification of sensed cardiac events vs. oversensing of noise events in the first cardiac electrical signal is unreliable based on baseline analysis of the second cardiac electrical signal. If a lead integrity alert condition has not been detected and the VT is being redetected after therapy delivery, the redetected VT is confirmed at block 624 and another therapy is delivered at block 624 without further lead issue analysis by control module 80.

If a lead integrity alert condition has been detected causing an alert to be generated at block 608, however, control module 80 enables saturation event detection at block 610 for use in detecting a possible lead issue and controlling therapy delivery. At block 612, saturation events are detected based on criteria as described above if a lead alert condition has been detected. The polarity, duration and/or time stamp of a detected saturation event may be stored and/or positive and negative saturation event counters may be adjusted for tracking saturation events. If VT is being detected or redetected at block 614, e.g., based on an NID defined for initially detecting a VT episode or an NID defined for redetecting the VT episode after therapy delivery or other VT detection/redetection criteria, saturation events are analyzed at block 616. Tracked saturation events are evaluated to determine if lead issue criteria are satisfied, e.g., as described above in conjunction with FIG. 6. Saturation events detected before a delivered therapy upon initial VT detection and/or after a delivered therapy upon VT redetection may be used to determine if the lead issue criteria are satisfied.

In some examples, a cardiac electrical signal used to detect VT, e.g., a near-field EGM signal, is buffered and is available for post-processing after the lead integrity alert is generated. In this case, control module 80 may "look back" over a near-term interval and long-term interval from the time that the lead integrity alert is generated to determine if saturation events are detected and meet lead issue detection criteria at block 616 when VT is detected or redetected. In other examples, detection of saturation events occurs in real time after the lead integrity alert is generated at block 608 such that saturation event data is available for determining if lead issue criteria are met at block 616 when VT is detected or redetected.

If saturation events satisfy the lead issue detection criteria at block 616, VT therapy is withheld at block 626. If tracked saturation events do not satisfy lead issue detection criteria at block 616, the control module 80 proceeds to block 618 and performs noise analysis of a second cardiac signal only if the VT detection is an initial VT episode detection and not redetection of a VT episode after therapy delivery. If saturation events do not meet lead issue detection criteria and the VT detected at block 614 is a redetected VT ("no" branch of block 618), the redetected VT is confirmed and therapy is delivered.

In this way, saturation events are tracked for use in controlling therapy delivery when VT is detected and when VT is redetected after a lead integrity alert has been generated due to other oversensing criteria and/or lead impedance criteria being met. If a lead integrity alert has not be issued, control module 80 may rely on analysis of a second cardiac signal for determining if only an initial VT detection is false due to oversensing and for controlling whether a therapy is delivered. Therapy may be withheld after VT redetection only if a lead integrity alert has been generated and detected saturation events satisfy lead issue detection criteria in the example process of flow chart 600.

Thus, various examples of medical device apparatus and associated methods have been described for detecting a medical electrical lead issue and controlling therapy delivery. One of ordinary skill in the art will appreciate that various modifications may be made to the described embodiments without departing from the scope of the following claims.

The invention claimed is:

1. An implantable medical device, comprising:
sensing circuitry to receive a first cardiac electrical signal via electrodes carried by a medical electrical lead when the medical electrical lead is coupled to the implantable medical device;
therapy delivery circuitry to deliver a tachyarrhythmia therapy to a patient's heart; and
a control module coupled to the sensing circuitry and the therapy delivery circuitry and configured to:
detect one or more saturation events from the first cardiac electrical signal;
detect a tachyarrhythmia based at least in part on the first cardiac electrical signal;
responsive to detecting the tachyarrhythmia, compare the detected saturation events to lead issue criteria; and
withhold the tachyarrhythmia therapy when the lead issue criteria are satisfied.

2. The device of claim 1, wherein the control module is configured to detect the saturation events by:
detecting one of a positive saturation amplitude and a negative saturation amplitude of the first cardiac electrical signal;
counting consecutive sample points of the first cardiac electrical signal that occur at or above the detected one of the positive saturation amplitude and the negative saturation amplitude;
comparing the sample point count to a saturation event threshold;
detecting the saturation event when the sample point count reaches the saturation event threshold.

3. The device of claim 1, wherein the control module is configured to:
store a polarity of each of the detected saturation events; and determine that the lead issue criteria are met when at least one of the detected saturation events is positive and at least one of the detected saturation events is negative.

4. The device of claim 1, wherein the control module is configured to:
   detect the tachyarrhythmia in response to analyzing the first cardiac electrical signal over a first time interval;
   compare saturation events detected during the first time interval to a first lead issue criterion of the lead issue criteria;
   compare saturation events detected during a second time interval to a second lead issue criterion of the lead issue criteria, the second time interval being longer than the first time interval and extending earlier in time from a time that the tachyarrhythmia is detected than the first time interval; and
   determine that the lead issue criteria are satisfied in response to both the first lead issue criterion and the second lead issue criterion being satisfied.

5. The device of claim 4, wherein the control module is further configured to:
   determine that the first lead issue criterion is satisfied when at least one saturation event is detected during the first time interval; and
   determine that the second lead issue criterion is satisfied when at least one saturation event having a positive polarity and at least one saturation event having a negative polarity are detected during the second time interval.

6. The device of claim 5, wherein the control module is configured to:
   determine a saturation event duration for each of the saturation events;
   compare a variation of the saturation event durations to an irregularity criterion; and
   determine that the lead issue criteria are met when the first lead issue criterion is satisfied, the second lead issue criterion is satisfied, and the variation of the saturation event durations satisfy the irregularity criterion.

7. The device of claim 1, wherein the control module is configured to:
   determine a saturation event duration for each of the saturation events;
   compare a variation of the saturation event durations to an irregularity criterion; and
   determine that the lead issue criteria are met when the variation of the saturation event durations satisfy the irregularity criterion.

8. The device of claim 1, wherein the control module is further configured to:
   detect a lead integrity alert condition; and
   enable the detecting of the saturation events in response to detecting the lead integrity alert condition.

9. The device of claim 1, wherein the control module is further configured to:
   control the therapy delivery circuitry to deliver the tachyarrhythmia therapy when the lead issue criteria are not satisfied;
   detect next saturation events after the therapy is delivered;
   redetect the tachyarrhythmia after the therapy is delivered;
   compare at least one of the detected saturation events and the next saturation events to the lead issue criteria in response to the tachyarrhythmia being redetected; and
   withhold a next therapy in response to the lead issue criteria being satisfied.

10. The device of claim 1, wherein:
    the sensing circuitry receives a second cardiac electrical signal; and
    the control module is configured to:
       analyze the second cardiac electrical signal in response to detecting the tachyarrhythmia from the first cardiac electrical signal if the tachyarrhythmia detection is an initial detection of a tachyarrhythmia episode;
       determine if the initial detection is due to noise oversensing in response to the analyzing of the second cardiac electrical signal;
       withhold the therapy in response to the initial detection being due to noise oversensing;
       redetecting the tachyarrhythmia episode; and
       determining if the lead issue criteria are satisfied by the detected saturation events when the tachyarrhythmia episode is redetected.

11. The device of claim 1, wherein:
    the sensing circuitry receives a second cardiac electrical signal; and
    the control module is configured to:
       detect a lead integrity alert condition;
       enable detection of the saturation events in response to detecting the lead integrity alert condition;
       determine if the lead issue criteria are satisfied when the tachyarrhythmia detection is an initial detection of a tachyarrhythmia episode;
       withhold the therapy in response to the lead issue criteria being satisfied;
       analyze the second cardiac electrical signal when the tachyarrhythmia detection is an initial detection of the tachyarrhythmia episode and the lead issue criteria are not satisfied;
       determine if the initial detection is due to noise oversensing in response to the analyzing of the second cardiac electrical signal;
       control the therapy delivery circuitry to deliver the tachyarrhythmia therapy when the initial detection is not due to noise oversensing and the lead issue criteria are not satisfied;
       redetect the tachyarrhythmia episode after the therapy is delivered;
       detect next saturation events after the therapy is delivered;
       compare at least one of the detected saturation events and the next saturation events to the lead issue criteria in response to the tachyarrhythmia being redetected; and
       withhold a next therapy in response to the lead issue criteria being satisfied.

12. A method, comprising:
    receiving a cardiac electrical signal by a sensing circuitry of an implantable medical device via electrodes carried by a medical electrical lead when the medical electrical lead is coupled to the implantable medical device;
    detecting one or more saturation events from the cardiac electrical signal by a control module of the implantable medical device;
    detecting a tachyarrhythmia based at least in part on the cardiac electrical signal;
    responsive to detecting the tachyarrhythmia, comparing the detected saturation events to lead issue criteria; and
    withholding a tachyarrhythmia therapy when the lead issue criteria are satisfied.

13. The method of claim 12, wherein detecting one of the saturation events comprises:

detecting one of a positive saturation amplitude and a negative saturation amplitude of the cardiac electrical signal;
counting consecutive sample points of the first cardiac electrical signal that occur at or above the detected one of the positive saturation amplitude and the negative saturation amplitude;
comparing the sample point count to a saturation event threshold; and
detecting the saturation event when the sample point count reaches the saturation event threshold.

14. The method of claim 12, further comprising:
storing a polarity of each of the detected saturation events; and
determining that the lead issue criteria are met when at least one of the detected saturation events is positive and at least one of the detected saturation events is negative.

15. The method of claim 12, further comprising:
detecting the tachyarrhythmia in response to analyzing the first cardiac electrical signal over a first time interval;
comparing saturation events detected during the first time interval to a first lead issue criterion of the lead issue criteria;
comparing saturation events detected during a second time interval to a second lead issue criterion of the lead issue criteria, the second time interval being longer than the first time interval and extending earlier in time from a time that the tachyarrhythmia is detected than the first time interval; and
determining that the lead issue criteria are satisfied in response to both the first lead issue criterion and the second lead issue criterion being satisfied.

16. The method of claim 15, further comprising:
determining that the first lead issue criterion is satisfied when at least one saturation event is detected during the first time interval; and
determining that the second lead issue criterion is satisfied when at least one saturation event having a positive polarity and at least one saturation event having a negative polarity are detected during the second time interval.

17. The method of claim 16, further comprising:
determining a saturation event duration for each of the detected saturation events;
comparing a variation among the saturation event durations to an irregularity criterion; and
determining that the lead issue criteria are met when the first lead issue criterion is satisfied, the second lead issue criterion is satisfied, and the variation among the saturation event durations satisfy the irregularity criterion.

18. The method of claim 12, further comprising:
determining a saturation event duration for each of the detected saturation events;
comparing a variation among the saturation event durations to an irregularity criterion; and
determining that the lead issue criteria are met when the variation among the saturation event durations satisfy the irregularity criterion.

19. The method of claim 12, further comprising:
detecting a lead integrity alert condition; and
enabling the detecting of the saturation events in response to detecting the lead integrity alert condition.

20. The method of claim 12, further comprising:
delivering the therapy when the lead issue criteria are not satisfied;
detecting next saturation events after the therapy is delivered;
redetecting the tachyarrhythmia after the therapy is delivered;
comparing at least one of the detected saturation events and the next saturation events to the lead issue criteria in response to the tachyarrhythmia being redetected; and
withholding a next therapy in response to the lead issue criteria being satisfied.

21. The method of claim 12, further comprising:
receiving a second cardiac electrical signal by the sensing circuitry;
analyzing the second cardiac electrical signal in response to detecting the tachyarrhythmia if the tachyarrhythmia detection is an initial detection of a tachyarrhythmia episode;
determining if the initial detection is due to noise oversensing in response to the analyzing of the second cardiac electrical signal;
withholding the therapy in response to the initial detection being due to noise oversensing;
redetecting the tachyarrhythmia episode; and
determining if the lead issue criteria are satisfied by the detected saturation events when the tachyarrhythmia episode is redetected.

22. The method of claim 12, further comprising:
receiving a second cardiac electrical signal by the sensing circuitry;
detecting a lead integrity alert condition;
enabling detection of the saturation events in response to detecting the lead integrity alert condition;
determining if the lead issue criteria are satisfied when the tachyarrhythmia detection is an initial detection of a tachyarrhythmia episode;
withholding the therapy in response to the lead issue criteria being satisfied;
analyzing the second cardiac electrical signal when the tachyarrhythmia detection is an initial detection of the tachyarrhythmia episode and the lead issue criteria are not satisfied;
determining if the initial detection is due to noise oversensing in response to the analyzing of the second cardiac electrical signal;
delivering the therapy when the initial detection is not due to noise oversensing and the lead issue criteria are not satisfied;
redetecting the tachyarrhythmia episode after the therapy is delivered;
detecting next saturation events after the therapy is delivered;
comparing at least one of the detected saturation events and the next saturation events to the lead issue criteria in response to the tachyarrhythmia being redetected; and
withholding a next therapy in response to the lead issue criteria being satisfied.

23. A non-transitory computer readable storage medium comprising instructions which when executed by a processor of an implantable medical device cause the implantable medical device to:
detect one or more saturation event from a cardiac electrical signal received by the implantable medical device via electrodes carried by a medical electrical lead when the medical electrical lead is coupled to the implantable medical device;

detect a tachyarrhythmia based at least in part on the cardiac electrical signal;

responsive to detecting the tachyarrhythmia, compare the detected saturation events to lead issue criteria; and withhold a tachyarrhythmia therapy when the lead issue criteria are satisfied.

* * * * *